United States Patent [19]

Comai et al.

[11] 4,302,450

[45] Nov. 24, 1981

[54] POLYETHER IONOPHORES AS ANTIOBESITY AND HYPOTRIGLYCERIDEMIC AGENTS

[75] Inventors: Karen Comai, Nutley; Ann Sullivan; John Westley, both of Cedar Grove, all of N.J.

[73] Assignee: Hoffmann-La Roche Inc., Nutley, N.J.

[21] Appl. No.: 123,537

[22] Filed: Feb. 22, 1980

Related U.S. Application Data

[62] Division of Ser. No. 3,158, Jan. 15, 1979, Pat. No. 4,218,443.

[51] Int. Cl.³ .................. A61K 31/35; A61K 31/40; A61K 31/60; A61K 31/71
[52] U.S. Cl. ................... 424/181; 424/230; 424/272; 424/274; 424/283; 424/285
[58] Field of Search ............ 424/181, 283, 230, 272, 424/285

[56] References Cited

U.S. PATENT DOCUMENTS

| | | | |
|---|---|---|---|
| 3,715,372 | 2/1973 | Stempel et al. | 424/115 |
| 3,944,573 | 3/1976 | Westley | 424/285 |
| 4,083,968 | 4/1978 | Westley | 424/181 |
| 4,161,520 | 7/1979 | Osborne et al. | 424/230 |

OTHER PUBLICATIONS

The Obese Patient, vol. IX, Bray, pp. 353 & 398–410, (1976).

*Primary Examiner*—Douglas W. Robinson
*Attorney, Agent, or Firm*—Jon S. Saxe; Bernard S. Leon; Frank P. Hoffman

[57] ABSTRACT

A method is disclosed for the use of polyether ionophores as antiobesity and hypotriglyceridemic agents in warm blooded animals by the administration to an animal in need of such treatment of a therapeutically effective dose of a polyether compound. Also disclosed are examples of such polyether compounds and methods for their preparation.

12 Claims, 2 Drawing Figures

FIG. 1

FIG. 2

POLYETHER IONOPHORES AS ANTIOBESITY AND HYPOTRIGLYCERIDEMIC AGENTS

This is a division of application Ser. No. 3,158 filed Jan. 15, 1979, now U.S. Pat. No. 4,218,443, issued Aug. 19, 1980.

BACKGROUND OF THE INVENTION

The present invention relates to a method of use of polyether ionophores as antiobesity and hypotriglyceridemic agents.

Obesity represents a state of increased body fat which may decrease longevity, aggravate the onset and progression of other diseases, e.g., heart disease, diabetes, gall stones, for example, and impact on one's social or economic status. [The Obese Patient, G. A. Bray, Vol. IX in the series "Major Problems in Internal Medicine", W. B. Saunders Co., 1976].

Plasma triglycerides are risk factors for ischemic heart disease, e.g. atherosclerosis. [The Heritable Hypolipoproteinemias and Atherosclerosis, C. J. Glueck and R. W. Fallat, Lipids, Lipoproteins and Drugs, pp 169–183 and 305–316, Plenum Press, 1975].

Thus an agent which exhibits activity in the reduction of obesity and the lowering of triglyceride levels would have a significant positive effect on heart disease, diabetes, gall stones, for example, through preventative measures.

Polyether ionophores are compounds which facilitate the transport of monovalent or divalent cations across a membrane. The "polyether" nature of the ionophore refers to the considerable number of tetrahydro-pyrans and -furans found in the ionophore structure. For the most part, these compounds have been found to exhibit weak antibiotic activity. Other utilities for many of these compounds include activities as growth promotants (U.S. Pat. No. 3,839,557), coccidiostatic agents (U.S. Pat. Nos. 3,719,753 and 3,577,531) and cardiovascular agents (U.S. Pat. No. 3,873,715).

The following compilation represents typical polyether compounds which exhibit an ionophoric effect and are useful in treating obesity and high triglyceride levels. The formulas which follow utilize the shorthand notations Me and Et which represent methyl and ethyl, respectively.

Nigericin

Nigericin has been known for some time under the names helixin C, antibiotic X-464, antibiotic K-178, polyetherin A, and azalomycin M. Its structure was characterized by Steinrauf et al., Biochemical and Biophysical Research Communications 33, 29 (1968). Harnes et al., Antibiotic and Chemotherapy I, 594–96 (1951) originally mentioned nigericin. It was also described by Gorman et al. in U.S. Pat. No. 3,555,510.

The organism which produces nigericin is a strain of *Streptomyces violaceoniger* which is on unrestricted deposit under identification number NRRL B1356 in the Northern Research and Utilization Development Division, Agricultural Research Service, U.S. Dept. of Agriculture, Peoria, Ill. The preparation of nigericin is described in U.S. Pat. Nos. 3,794,732 and 3,839,557.

Monensin    $R_1=CH(Me)CO_2H, R_2=Me, R_3=Et$
Factor B    $R_1=CH(Me)CO_2H, R_2, R_3=Me$
Factor C    $R_1=(CH_2)_3CO_2H, R_2=Me, Me$
Factor D    $R_1=CH(Me)CO_2H, R_2=Et, R_3=Me$ Monensin was described by Haney et al., U.S. Pat. No. 3,501,568. The substance commonly known as monensin or A 3823 complex is actually a mixture of four components. These four components are included in the term "monensin" as used herein.

Monensin is the fermentation product of an organism which can be found on unrestricted deposit under the number ATCC 15413 in the American Type Culture Collection, Rockville, Md. A method of production for the monensin complex is disclosed in U.S. Pat. No. 3,501,568.

Also within the ambit of the present invention are the metabolites of monensin such as A-27106 disclosed and claimed in U.S. Pat. No. 3,932,619. A-27106 is produced from the conversion of monensin by an enzyme system produced by an organism *Streptomyces candidus* available as accession number NRRL 5449 at Northern Regional Research Laboratories, Peoria, Ill.

Antibiotic X-206

The compound X-206 was reported for the first time in 1951 by Berger et al., JACS 73, 5295–98 (1951). The Streptomyces organism from which one is able to obtain antibiotic X-206 is available at Center International d'Information sur Les Antibiotiques (International Center for Information on Antibiotics) Liege, Belgium, which lists the organism on page 31 of its Bulletin No. 3 (1966). Its formula has been characterized by Blount et al., Chemical Communications (London), p. 533, 1975. A method for the preparation of X-206 is disclosed in U.S. Pat. Nos. 3,794,732 and 3,839,557.

Salinomycin

The compound Grisorixin was first reported in 1970 by Gachon et al., Chem. Commun., P 1421 (1970). The compound was found to differ by only a single oxygen atom from nigericin. The Streptomyces organism from which one is able to obtain the compound Grisorixin is *Streptomyces griseus*. A method for the preparation of Grisorixin is shown in the Gachon et al. article.

Laidlomycin

The compound Salinomycin was first reported in 1973 by Kinahsi et al., Tetrahedron Letters, 49, 4955 (1973). Salinomycin is the fermentation product of an organism (*Streptomyces albus*) which can be found on unrestricted deposit under Number ATCC 21838 in the American Type Culture Collection, Rockville, Md. and from the Fermentation Research Institute in Japan as *Streptomyces albus* 80, 614 (No. 419). A method of producing Salinomycin by fermentation is disclosed by Tanaka et al. in U.S. Pat. No. 3,857,948. Related compounds to salinomycin have also been reported in the literature, for example, Deoxy-(0-8)-salinomycin by Shibata et al., Japanese Pat. No. 51-8619; Salinomycin II by Yonehara et al., Japanese Pat. No. 50-132190; and the C-17 epimer of deoxy-(0-8)-salinomycin by Westley et al., Journal of Antibiotics, 30, 610 (1977).

Grisorixin

$R_1=CH(Me)CO_2H, R_2=Me$

The compound "laidlomycin" and a method for its production has been disclosed by Kitame et al. in the Journal of Antibiotics, Vol. XXVII No. 11, pp. 884–888, 1974. The compound is produced by the fermentation of a *Streptomyces eurocidicus* var. asterocidius (similar) assigned the designation Streptomyces S-822. This species is indexed as S-822 at the Department of Bacteriology, Tohoku University School of Medicine, Sendai, Japan.

Dianemycin

The compound Dianemycin was first reported in 1971 by Czerwinski et al., Biochem. Biophys. Res. Commun., 45, 1284 (1971). Dianemycin is the fermentation product of an organism (*Streptomyces hygroscopicus*) which can be found on unrestricted deposit under number NRRL 3444 in the Northern Research and Utiliza- tion Development Division, Agricultural Research Service, U.S. Dept. of Agriculture, Peoria, Ill. A method for its preparation is disclosed in U.S. Pat. No. 3,577,531 to Gorman et al.

plex is disclosed in Belgium Pat. No. 830,043 published Dec. 10, 1975.

Lonomycin A
(TM-481)

Lenoremycin (Antibiotic A-130A)

The compound A-130A was discovered by Oikawa et al. and is disclosed together with a method for its production in U.S. Pat. No. 3,903,264 issued Sept. 2, 1975. The compound is produced by the fermentation of a strain of *Streptomyces hygroscopicus* available to the public under the accession number ATCC 21840 at the American Type Culture Collection in Rockville, Md.

Recently, Blount et al. in Chemical Comm. (London), pp. 853–855 (1975) have provided a structural elucidation of this compound.

A 28086
  Factor A ($R_1=R_2=Me$, $R_3=OH$
  Factor B ($R_1$, $R_2=Me$; $R_3=O$
  Factor D ($R_1$, $R_2=Me$, Et; $R_3=OH$)

The antibiotic lonomycin was first reported and elucidated structurally by Omura et al. in Journal of Antibiotics, Vol. XXIX, No. 1, pp. 15–20, Jan. 1976 and Otake et al., Tet. Letters No. 47, pp. 4147–4150, 1975. The antibiotic is produced by a *Streptomyces ribosidificus* strain TM-481 which is deposited as ATCC No. 31051 at the American Type Culture Collection in Rockville, Md. A method of producing the antibiotic by fermentation is disclosed by Sawada et al. in U.S. Pat. No. 3,950,514. Subsequent publications by Riche et al. (as Emericid) in Chem. Comm. (London), pp 951–952 (1975) and Benazet et al. (as 31599 RP) at the 9th International Congress of Chemotherapie in London, July 13–18, 1975 disclosed identical compounds to lonomycin. Lonomycins B and C have also been disclosed Antibiotic complex A 28086 is made up of at least three components, one of which, factor A, is known as narasin. The complex is produced by fermentation of an organism, *Streptomyces aureofociens* which can be found on deposit in the Northern Regional Research Laboratories in Peoria, Ill. under NRRL numbers 8092 or 5758. A method of fermentation to produce the A 28086 comalong with their structures by H. Seto et al., in Journal of Antibiotics, 31, 929 (1978b).

Alborixin

The compound Alborixin was first reported by M. Alleaume et al., Chem. Comm. (London), pp 411–412 (1975). The compound is obtained by the fermentation of a strain of *Streptomyces albus* sp. 3840 as reported by Delhomme et al. in Journal of Antibiotics, Vol. XXIX, No., 7, pp 692–695 (1976).

Septamycin

The compound Septamycin also known as A 28695 together with A 28695B was first described in U.S. Pat. No. 3,839,558 to Hamill et al. The structure was elucidated by T. J. Petcher et al., Chem. Comm., (London) 697 (1974). Septamycin differs from A-204A (below) in the loss of one of the five methoxyls present in A-204A and a change in the configuration and the point of attachment of the glycoside-like branched tetrahydropytonyl ring. Septamycin is obtained by the fermentation of a strain of *Streptomyces hydroscopicus* as disclosed in the above mentioned patent.

Antibiotic A-204A

The compound A-204A was reported for the first time by N. D. Jones et al., J. Amer. Chem. Soc., 95, 3399 (1973). It is obtained by the fermentation of a strain of the organism *Streptomyces albus*. This strain is found on unrestricted deposit under the number NRRL 3384 in the Northern Research and Utilization Development Division, Agricultural Research Service, U.S. Dept. of Agriculture, Peoria, Ill. A method for the production of A-204A (I) is disclosed in U.S. Pat. No. 3,705,238. U.S. Pat. Nos. 3,953,474 and 3,907,832 also disclose information on the above antibiotic which is disclosed as a complex.

Antibiotic 38295

The compound antibiotic 38295 was first reported by Celmer et al., in Belgium Pat. No. 831,947 published on Feb. 2, 1976. The patent discloses a method of production for the antibiotic by fermentation of the organism *Streptomyces hygroscopicus* found on deposit under the number ATCC 31050 in the American Type Culture Collection, Rockville, Md.

Lasalocid A  $R_1=R_2=R_3=R_4=Me$
Lasalocid B  $R_1=Et, R_2=R_3=R_4=Me$
Homolog C  $R_2=Et, R_1=R_3=R_4=Me$
Homolog D  $R_3=Et, R_1=R_2=R_4=Me$ Homolog E  R₄=Et,R₁=R₂=R₃=Me
Iso-Lasalocid A R = Me Noboritomycin A
R = Et Noboritomycin B

The compound Lasalocid A, its isomer and its homologs are produced by the fermentation of the organism *Streptomyces lasaliensis*. The organism can be found on unrestricted deposit under the number NRRL 3382 in the Northern Research and Utilization Development Division, Agricultural Research Service, U.S. Dept. of Agriculture, Peoria, Ill. and under the number ATCC 31180 in the American Type Culture Collection, Rockville, Md. The compound Lasalocid A, its isomer and its homologs have been first reported by Berger et al., J. Amer. Chem. Soc., 73, 5295 (1951), J. Westley et al., J. Antibiot., 27, 597 (1974) and J. Westley et al., J. Antibiot., 27, 744 (1974) respectively. Also disclosed in these articles are methods for the preparation of the respective compounds.

Lysocellin

The compound Lysocellin was first reported by Ebata et al. in J. Antibiotic., 28, 118–121 (1975). The compound is produced by fermentation of a *Streptomyces cocaoi* var. asoensis K-9 Met. mutant. It has also been found this compound, also known as X-14537A, can be produced by fermentation of a *Streptomyces longwoodensis* which is deposited as ATCC 20251 at the American Type Culture Collection in Rockville, Md. and the fermentative method disclosed in Int. J. of Systematic Bacteriology, Vol. 26 (3), pp 310–322, 1976 article by Palleroni et al.

Mutalomycin

The compound Mutalomycin is described by Fehr et al. in the Journal of Antibiotics, 30, pp 903–907, 1977. The antibiotic is the product of the fermentation of the *Streptomyces mutabilis* deposited as NRRL 8088 at the Northern Regional Research Laboratories.

Noboritomycin A and B

Noboritomycin A and B are disclosed as produced by the fermentation of the organism *Streptomyces noboritoensis* deposited as NRRL 8123 at the Northern Regional Research Laboratories, Peoria, Ill.

Antibiotic A23187 (Calcimycin)

The compound A 23187 was first reported by M. O. Chaney et al., J. Amer. Chem. Soc., 96, 1932 (1974) as containing two cyclic ethers in a spiro ring system and a carboxylic acid function. The molecular formula was calculated as $C_{29}H_{37}N_3O_6$. The compound is obtained by the fermentation of a strain of *Streptomyces chartreusensis*. A method of preparation of A 23187 by fermentation of the *Streptomyces chartreusensis* is set forth in U.S. Pat. No. 3,923,823 to Gale et al. The organism is on deposit at the Northern Regional Research Laboratories, Peoria, Ill. as NRRL 3882.

Antibiotic X-14547A

K-41 (A-32887)

Antibiotic X-14547 is disclosed in U.S. Pat. No. 4,100,171 issued July 11, 1978 to Westley et al. The compound is obtained by fermentation of the organism *Streptomyces antibioticus* deposited as NRRL 8167 at the U.S. Department of Agriculture, Agricultural Research Service, Northern Regional Research Laboratories, Peoria, Ill. A structure for the compound is disclosed in the patent.

Carriomycin (T-42082)

The compound "K-41" and a method for its production has been disclosed by Tsuzi et al. in the Journal of Antibiotics, Vol. XXIX, No. 1, pp 10-14, 1976. The compound is produced by the fermentation of a *Streptomyces hygroscopicus* given the designation FERM-P 1324 and on deposit at the Fermentation Research Institute, agency of Industrial Science and Technology, Chiba, Japan. Further information can be found in J.C.S. Chem. Comm., 682–683 and 683–684(1978).

CP44161

CP44,161 is disclosed in U.S. Pat. No. 4,081,532 issued Mar. 28, 1978 to Celmer et al. The compound is obtained by the fermentation of the organism *Dactylosporangium aurantiacum* deposited as ATCC 23491, and *Dactylosporangium salmoneum* deposited as 31222,31223 and 31224 at the American Type Culture Collection, Rockville, Maryland. IR spectra of the antibiotic is disclosed.

BL-580 Δ

Carriomycin is disclosed in U.S. Pat. No. 4,069,316 to Imada et al. The compound is produced by the fermentation of the organism *Streptomyces hydgroscopicus* T-42082 deposited as ATCC 31080 at the American Type Culture Collection, Rockville, Md. I.R. and N.M.R. data for the antibiotic are disclosed.

BL 580 Δ is disclosed in Belgian Pat. No. 856,314 issued Dec. 30, 1977. The fermentation of the antibiotic is carried out by a strain of *Streptomyces hygroscopicus* deposited as NRRL 8180.

Polyether Ionophore Compounds of Unknown Structure

Ionomycin

Ionomycin is disclosed in U.S. Pat. No. 3,873,693 to Meyers et al. The compound is obtained by fermentation of an organism *Streptomyces conglobatus* deposited as ATCC 31005 at the American Type Culture Collection, Rockville, Md. Characterization of the compound by I.R. and U.V. spectra are disclosed in the patent.

CP 38,986

CP 38,986 is disclosed in U.S. Pat. No. 4,002,885 to Celmer et al. The compound is obtained by the fermentation of the organism *Streptomyces flaveolus* deposited as ATCC 31100 at the American Type Culture Collection, Rockville, Md. Characterization of the compound by I.R. spectra is disclosed in the patent.

30,504RP 30,504RP is disclosed in U.S. Pat. No. 3,989,820 issued Nov. 2, 1976 to Florent et al. The compound is obtained by the fermentation of the organism *Streptomyces gallinarius* DS25881 deposited as NRRL 5785 at the Northern Regional Research Laboratories, Peoria, Ill. Characterization data in the form of an I.R. spectrum is disclosed.

Antibiotics BL-580 α and β disclosed in U.S. Pat. No. 3,812,249 to Martin et al. have been found to be identical to the previously disclosed A28695 A and B.

Considered within the ambit of the present invention are the organic or inorganic pharmaceutically acceptable salts of the polyether compounds. These salts are prepared from the free acid methods well known in the art, for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like, alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonate and sulfates. Preferred for use in this invention are salts formed from alkali metal bases.

Examples of organic bases forming pharmaceutically acceptable salts with the polyether compounds are lower alkyl amines, primary, secondary and tertiary hydroxy-lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water solubility which makes them amenable to parenteral use.

Also considered within the ambit of the present invention are the derivatives of the polyether compounds Lasalocid A, its isomers and homologs. Disclosure of these derivatives and teaching of their preparation and identity may be found, for example, in U.S. Pat. Nos. 3,715,372 issued Feb. 6, 1973; 3,944,573 issued Mar. 16, 1976 and 3,836,516 issued Sept. 17, 1974. These patents are herewith incorporated by reference for completeness of disclosure in the present application.

Esters of lasalocid should also be considered within the ambit of the present invention, i.e., $C_2$ to $C_{10}$ alkyl and benzoyl or substituted, e.g., vitro, halo or $C_1$ to $C_7$ alkyl, benzoyl esters on the phenolic hydroxyl group of lasalocid. Such esters may be formed by methods known in the art, for example, U.S. Pat. No. 3,715,372.

For use as antiobesity and hypotriglyceridemic agents, the active agents are formulated using conventional inert pharmaceutical adjuvant materials into dosage forms which are suitable for oral administration. Other dosage forms, e.g., parenteral, may be possible. The oral dosage forms include tablets, capsules, dragees, suspensions, solutions and the like. The identity of the inert adjuvant materials which are used in formulating the active ingredients into oral dosage forms will be immediately apparent to persons skilled in the art. These adjuvant materials, either inorganic or organic in nature, include, for example, gelatin, albumin, lactose, starch, magnesium stearate, preservatives (stabilizers), melting agents, emulsifying agents, salts for altering osmotic pressure, buffers, etc., which can be incorporated, if desired, into such formulations.

A suitable pharmaceutical dosage level can be about 1 mg/kg/day to 300 mg/kg/day with 1 mg/kg/day to 100 mg/kg/day as preferred. Such dosage levels would be effective in treating obesity or hypertriglyceridemia in mammals. The dosage administered to a particular individual should be varied within the above dosage range based on the efficacy and possible side effects of the particular polyether ionophore chosen. The desired antiobesity or hypotriglyceridemic effect must be a function of the particular compound's potency and the weight and physical condition of the individual patient. Therefore, an effective dosage amount of active compound can only be determined by the clinician utilizing his best judgment on the patient's behalf.

The ionophores of the present invention can also be compounded or blended with a feed additive, premix, feed concentrate or feed additive supplement to form a dietary admixture for administration to an animal. A feed additive, concentrate or premix is a composition to be diluted to produce a complete feed, i.e., a composition to be administered as a sole ration. A feed additive supplement is a composition to be consumed directly by the animal or which can be further diluted to produce a complete feed or which can be ingested and used as a supplement to other rations. Dietary admixtures usually contain a relatively large percentage of ionophores, i.e., the active ingredient, and are conveniently prepared by adding the active ingredient to a suitable carrier and mixing, so as to assume a substantially uniform dispersion of the ionophore in the carrier. Suitable carriers are solids that are inert with respect to the active ingredient and which may safely be ingested by the animals to be treated. Typical of such carriers are commercial animal feeds, ground cereal grains, grain by-products, plant protein concentrates (soy, peanuts, etc.), fermentation by-products, salt, limestone, inorganic compounds, and the like or mixtures thereof. Liquid dispersions can be prepared by using water or vegetable oil, preferably including a surface active agent, emulsifying agent, and the like in the liquid dispersion such as ethylenediamine tetraacetic acid, etc. and solubilizers. Any suitable carrier or extender material can function as the inert ingredient in the solid form of the antiobesity and hypotriglyceridemic agent provided that it is inert to the active material and is non-toxic insofar as the animal to which it is to be administered is concerned.

The active ingredient may be blended into a mash, pellet or any desired configuration with the inert carrier or extender solid material by any convenient technique. For example, compositions can be formed by finely grinding or pulverizing the active ingredient and the inert ingredient using any commercially available grinder or pulverizer with or without the feed material being present. If the feed material is not present when the grinding or pulverizing is effected, the resultant material can be distributed, in accordance with the present invention, in any conveniently available feed material. Typical animal feeds which can be medicated with the active ingredient of this invention can contain several ingredients, for example, they can contain high energy grain products such as corn, wheat, wheat red dog flour, milo, oatmeal or the like; medium and low energy grain products such as oats, barley, wheat flour, middlings, standard middlings or the like; stabilized fats; vegetable protein such as soybean meal, corn gluten metal, peanut meal or the like; animal protein such as fish meal, fish solubles, meat scraps or the like; UGF (unidentified growth factor) sources and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline, vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone or the like; iodized salt, manganese sulfate, zinc carbonate, and antibiotic feed supplement, methionine or its hydroxy analog and an antioxidant.

The antiobesity and hypotriglyceridemic effects are confirmed by in vitro and in vivo inhibition of pancreatic lipase, lipoprotein lipase, fatty acid synthesis and the measurements of decreased amounts of body fat and serum triglycerides.

The following examples illustrate the antiobesity and hypotriglyceridemic activities of the polyether ionophores.

EXAMPLE 1

Pancreatic lipase preparation:

Pancreatic lipase was prepared from Charles River female rats by adapting the method of Scheele and Palade for the guinea pig pancreas, [G. A. Scheele and G. E. Palade (1975). Studies on the guinea pig pancreas, parallel discharge of exocrine enzyme activities, J. Biol. Chem., 250: 2660–2670]. The rats were fasted 24 hours prior to killing to accumulate zymogen granules in the acinar cells, [J. P. Reboud, A. B. Abdeljlil, and P. Desnuelle (1962). Variations De La Teneur en Enzymes Du Pancreas de Rat en Fonction De la Composition Des Regimes, Biochim. Biophys. Acta, 58: 326–337]. After killing the pancreas was removed quickly and immersed in oxygenated Krebs-Ringer bicarbonate and pancreatic lobules prepared as described by Scheele and Palade (supra) and stimulated to release pancreatic proteins by addition of $10^{-5}$ M carbachol. The resulting "juice" was centrifuged at $100,000 \times g$ in a refrigerated Beckman L2-65B centrifuge and frozen immediately in liquid nitrogen and stored at $-70°$ C., [K. Comai, J. Triscari, and A. C. Sullivan (1978). Differences between lean and obese Zucker rats: The effect of poorly absorbed dietary lipid on energy intake and body weight gain, J. Nutr., 108: 826–835]. Human pancreatic juice was obtained from a patient with acute pancreatitis whose pancreatic duct had been cannulated, human pancreatic juice was a gift from Dr. George Nardi, Massachusetts General Hospital, Boston.

In vitro pancreatic lipase assay:

The method for assaying pacreatic lipase in vitro using [$^{14}$C]-triolein was based on the method of Garfinkel and Schotz for lipoprotein lipase, [A. S. Garfinkel and M. C. Schotz (1972). Separation of molecular species of lipoprotein lipase from adipose tissue, J. Lipid Res., 13: 63–68]. Glycerol tri[1-$^{14}$C]oleate (32 mM) was emulsified in 0.2 M Tris-HCl pH 8 containing 0.15 M NaCl, bovine serum albumin (15 mg/ml) and sodium taurocholate (1.4 mM) by sonication for three, one min intervals at 80 watts. Final assay volume was 1.0 ml. The reaction was initiated by the addition of enzyme and was allowed to proceed for 10 min. The reaction was linear for up to 20 min. The liberated free fatty acids were extracted into 0.1 M KOH and quantitated in a liquid scintillation counter using 2,5-bis-2-(5tertbutyl-benzoxazoly)-thiophene (BBOT) scintillation fluid (Yorktown Research, South Hackensack, N.J.).

Ionophores were added to the above assay as solutions in either 90% ethanol or water, pH 8; 90% ethanol had no effect on the enzyme activity assayed by either method. The results are in Table I.

TABLE 1
ACTIVITY IN PANCREATIC LIPASE SCREEN: IONOPHORES

| Class | Compound | Pancreatic Lipase Activity $I_{50}$mM |
|---|---|---|
| Monovalent: | A-130A (Lenoremycin) | 0.15 |
| | A-204 | 0.16 |
| | BL-580 | 0.20 |
| | Deoxy-(0-8)-epi-17-salinomycin | 0.60 |
| | A28086 | 0.77 |
| | X-206 | 0.84 |
| | Ionomycin | 0.96 |
| | Nigericin | 2.5 |
| Divalent: | Lasalocid | 0.10 |
| | Lasalocid methoxime | 0.20 |
| | Iodolasalocid | 0.26 |
| | Isolasalocid A | 0.39 |
| | Dinitrodescarboxylasalocid | 0.40 |
| | Bromolasalocid | 0.60 |
| | Lysocellin | 0.80 |
| | Nitrolasalocid | 1.32 |
| | Chlorolasalocid | 7.0 |
| | Lasalocid Stearate | 0.11 |
| | Lasalocid Octanoate | 0.11 |
| | Lasalocid Acetate | 0.12 |
| | Lasalocid 4-bromo benzoate | 0.13 |
| | Lasalocid Hexanoate | 0.20 |
| | Lasalocid Heptanoate | 0.22 |
| Pyrrole Ethers: | X-14547A | 0.7 |

EXAMPLE 2

Pancreatic lipase preparation:

Pancreatic lipase was prepared from Charles River female rats by adapting the method of Scheele and Palade for the guinea pig pancreas, [G. A. Scheele and G. E. Palade (1975). Studies on the guinea pig pancreas, parallel discharge of exocrine enzyme activities, J. Biol. Chem., 250: 2660-2670]. The rats were fasted 24 hours prior to killing to accumulate zymogen granules in the acinar cells, [J. P. Reboud, A. B. Abdeljlil, and P. Desnuelle (1962). Variations De la Teneur en Enzymes Du Pancrease de Rat en Fonction De la Composition Des Regimes, Biochim. Biophys. Acta, 58: 326-337]. After killing the pancreas was removed quickly and immersed in oxygenated Krebs-Ringer bicarbonate (see Scheele and Palade above). Pancreatic lobules were prepared as described by Scheele and Palade (supra) and stimulated to release pancreatic proteins by additon of $10^{-5}$ M carbachol. The resulting "juice" was centrifuged at 100,000 × g in a refrigerated Beckman L2-65B centrifuge and frozen immediately in liquid nitrogen and stored at −70° C., [K. Comai, J. Triscari, and A. C. Sullivan (1978). Differences between lean and obese Zucker rats: The effect of poorly absorbed dietary lipid on energy intake and body weight gain, J. Nutr., 108: 826-835]. Human pancreatic juice was obtained from a patient with acute pancreatitis whose pancreatic duct has been cannulated, human pancreatic juice was a gift from Dr. George Nardi, Massachusetts General Hospital, Boston.

In vitro pancreatic lipase assay:

Pancreatic lipase activity was determined by the titrimetric assay described by Maylie et al., [M. F. Maylie, M. Charles and P. Desnuelle (1972). Action of organophosphates and sulfonylhalides on porcine pancreatic lipase. Biochim. Biophys. Acta, 276, 162-175]. An olive oil (6 mM or 28 MM)-sodium taurocholate (1.4 mM) emulsion stabilized in 2% gum arabic was used as substrate, [K. Comai, J. Triscari and A. C. Sullivan (1978). Comparative effects of amphetamine and fenfluramine on lipid biosynthesis and absorption in the rat. Biochem. Pharm., 27, 1987-1994]. The final assay volume was 3.0 ml. The reaction was initiated by the addition of enzyme. The longchain fatty acids released at pH 8 were continuously titrated with a recording pH-state (Radiometer, Copenhagen). The lipase activity (1 unit = 1-µmole free fatty acid released per minute) was determined directly from the slope of the curve. The data are expressed as µmoles of fatty acid released per minute. Inhibitory data were evaluated by the method of Dixon and $K_i$ values determined, [M. Dixon and E. C. Webb, in Enzymes, p. 329, Academic Press, New York (1964)].

Ionophores were added to the above assays as solutions in either 90% ethanol or water, pH 8; 90% ethanol had no effect on the enzyme activity assayed by either method.

Figure 1:
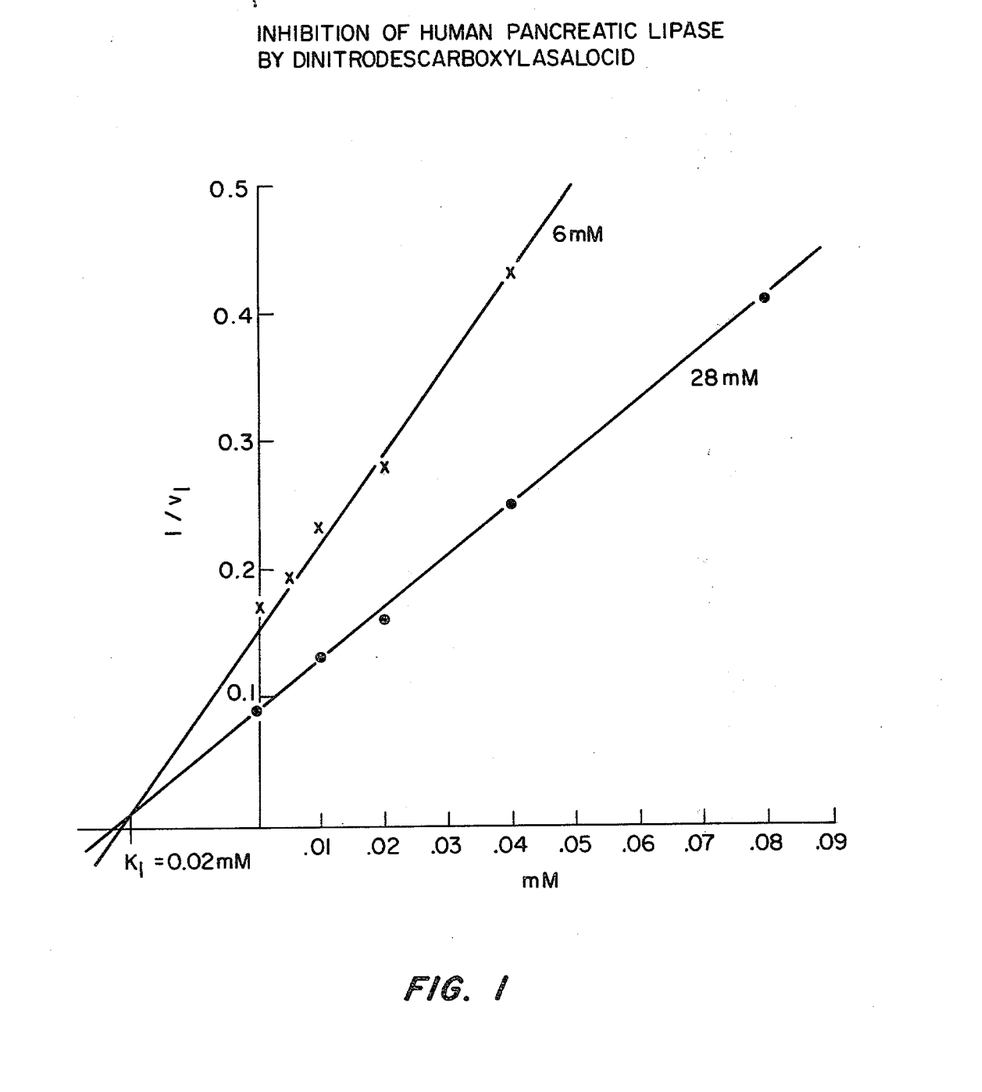

FIG. 1 sets forth Dixon plots of kinetic data gathered from an evaluation of dinitrodescarboxylasalocid in the in vitro Radiometer assay using human pancreatic lipase. An inhibition constant $(K_i)$ of 0.02 mM was determined from the Dixon plots for dinitrodescarboxylasalocid which suggested competitive inhibition. Table 2 sets forth the inhibition constants of bromolasalocid in the in vitro Radiometer assay using human pancreatic lipase.

TABLE 2
INHIBITION CONSTANTS FOR BROMOLASALOCID INHIBITION OF HUMAN PANCREATIC LIPASE

| Compound | $K_i$ mM |
|---|---|
| Bromolasalocid, Na+ | 0.05 |
| Bromolasalocid, Ethanolate | 0.10 |
| Bromolasalocid, di-(N-methylglucamine) | 0.16 |

EXAMPLE 3

In vitro lipoprotein lipase preparation and assay:

Acetone powders of Zucker rat epididyml adipose tissue were the source of lipoprotein lipase and were prepared by the method of Garfinkel and Schotz, [A. S. Garfinkel and M. C. Schotz (1972). Separation of molecular species of lipoprotein lipase from adipose tissue, J. Lipid Res., 13: 63-68]. The adipose tissue was removed quickly and immediately homogenized in acetone (15 ml per gram of adipose tissue) in a Waring Blender at high speed for one minute, then filtered quickly through a coarse fritted glass funnel. The extract was washed twice with acetone (3 ml per gram of adipose tissue), then washed two more times with anhydrous ethyl ether (3 ml per gram adipose tissue). The powder was dried under vacuum for one hour, weighed and stored desiccated at −70° C. Approximately 0.013 g acetone powder was obtained per gram of epididyml adipose tissue. The lipoprotein lipase was extracted from the acetone powder into 0.05 M $NH_4OH$—$NH_4Cl$ buffer, pH 8.6. The extracts were prepared by homogenizing the acetone powder in buffer in a TenBroeck glass tissue grinder in ice. The homogenate was centrifuged at 2,000 × g for 20 min to remove insoluble material.

Lipoprotein lipase was assayed in a manner similar to pancreatic lipase, [A. S. Garfinkel and M. C. Schotz (1972). Separation of molecular species of lipoprotein lipase from adipose tissue, J. Lipid Res., 13: 63-68]. [K. Comai, J. Triscari and A. C. Sullivan (1978). Differences between lean and obese Zucker rats: The effect of poorly absorbed dietary lipid on energy intake and body weight gain, J. Nutr., 108: 826-835]. Glycerol tri[1-$^{14}$C]oleate (8 μCi) and glycerol trioleate (15 mM) were emulsified with 1.5 mg lysophosphatidylcholine, 3 ml fasted rat serum, 0.5 ml of 1% bovine serum albumin and 2.4 ml of 0.2 M Tris-HCl, pH 8.0 by sonication for a total of three min in 30 second intervals at 80 watts. For each assay 0.6 ml of the above substrate was used; the final assay volume was 1.0 ml. The substrate was activated by preincubation at 37° C. for 30 min. The enzyme reaction was initiated by the addition of enzyme (usually 0.2 ml) and was allowed to proceed for 30 min. The reaction was linear up to 60 min. The liberated free fatty acids were extracted into a carbonate buffer, pH 10.5, and quantitated by liquid scintillation counting in Aquasol (New England Nuclear, Boston, Mass. Results are expressed as μmoles fatty acid released per hour.

Ionophores were added to the above assays as solutions in either water or DMSO. DMSO at amounts greater than 0.1 ml caused significant inhibition of lipoprotein lipase.

The dinitrodescarboxylasalocid acted as an inhibitor of rat epididynml lipoprotein lipase in the in vitro assay exhibiting an $I_{50}$ value of 0.27 mM.

In the following examples, female rats (Charles River CD strain, 180-200 g) were housed individually in wire bottom cages in a temperature (22°) and light (12 hr light and 12 hr dark) regulated room. They had free access to Purina Rodent Chow and water.

In meal-fed experiments Charles River rats were fasted 24 hr, then meal-fed a G-70 (70% glucose) diet for either two or three hours daily for 9-14 days prior to the experiments, [K. Comai, J. Triscari and A. C. Sullivan (1978). Differences between lean and obese Zucker rats: The effect of poorly absorbed dietary lipid on energy intake and body weight gain, J. Nutr., 108: 826-235].

Ad libitum fed lean and genetically obese Zucker rats (140 days old) were used in one chronic study.

EXAMPLE 4

In Vitro fatty acid synthesis:

Hepatocytes were prepared from meal-fed Charles River Female rats as described previously, [A. C. Sullivan, J. Triscari, J. G. Hamilton and J. A. Ontko (1977). Hypolipidemic activity of (−)-hydroxycitrate, Lipids, 12: 1-9]. Briefly, rats were anesthetized with Nembutal, livers were perfused in situ and hepatocytes were isolated in Krebs-Henseleit bicarbonate buffer, pH 7.4. Incubations with isolated hepatocytes were performed in triplicate at 37° C. Each incubation flask contained in a total volume of 2.1 ml, 10.5 mg cells (dry weight), 1 ml of Krebs-Henseleit buffer, pH 7.4, radioactive substrate (μCi[U-$^{14}$C]alanine, 1 mCi$^3$H$_2$O and 1 μmole alanine) and 0.3% glucose. The appropriate concentration of inhibitor was prepared in dimethylsulfoxide and added to the incubation flask. Dimethylsulfoxide had no effect on fatty acid synthesis. $^3$H$_2$O was used to determine the total rate of fatty acid synthesis independently of carbon precursors of acetyl CoA. [$^{14}$C]alanine was used as an acetyl CoA pressure. Rates of fatty acid synthesis were determined as described previously, [A. C. Sullivan, J. Triscari, J. G. Hamilton and J. A. Ontko (1977). Hypolipidemic activity of (−)-hydroxycitrate, Lipids, 12: 1-9]. Data are expressed as nmoles $^3$H$_2$O or [$^{14}$C]analine converted into fatty acids per mg dry weight cells in 60 minutes. The results are summarized in Table 3.

TABLE 3

EFFECT OF IONOPHORES ON FATTY ACID SYNTHESIS IN ISOLATED HEPATOCYTES

| Compound | Concentration mM | Fatty Acid Synthesis[a] $^3$H$_2$O % of control | [$^{14}$C]alanine % of control |
|---|---|---|---|
| Lasalocid, Sodium | 0.001 | 97 | 88 |
|  | 0.005 | 74* | 66* |
|  | 0.010 | 61* | 66* |
|  | 0.100 | 4* | 0* |
|  | 0.250 | 6* | 1* |
|  | 0.500 | 7* | 3* |
|  | 1.000 | 11* | 0* |
| Dinitrodescarboxylasalocid, Sodium | 0.001 | 113* | 102 |
|  | 0.005 | 116 | 117 |
|  | 0.010 | 160* | 169* |
|  | 0.100 | 2* | 0* |
|  | 0.250 | 3* | 0* |
|  | 0.500 | 3* | 0* |
|  | 1.000 | 4* | 0* |
|  | 2.000 | 7* | 0* |
| Bromolasalocid, Sodium | 0.5 | 14* | 0* |
|  | 1.0 | 22* | 0* |
| Calcimycin | 1.0 | 48* | 0* |

[a]Data are expressed as the percent of control of triplicate incubations.
*Significantly different from control P ≦ 0.05.

EXAMPLE 5

In Vivo fatty acid synthesis:

The test compound was administered either orally by intubation 30 min prior to the three hour G-70 meal or intraperitoneally immediately following the 3 hour meal, [K. Comai, J. Triscari and A. C. Sullivan (1978). Differences between lean and obese Zucker rats: The effect of poorly absorbed dietary lipid on energy intake and body weight gain, J. Nutr., 108: 826-835]. [A. C. Sullivan, J. Triscari, J. G. Hamilton and J. A. Ontko (1977). Hypolipidemic activity (−)-hydroxycitrate, Lipids, 12: 1-9]. Immediately after the meal for the oral experiment or 30 minutes following the meal for the intraperitioneal experiment a radioactive pulse consisting of 1 mCi$^3$H$_2$O, 5 uCi[U-$^{14}$C]-analine, 12.3-mg analine and 30.6 mgα-ketoglutarate was administered intraveneously in the tail vein, [A. C. Sullivan, J. Triscari, J. G. Hamilton and J. A. Ontko (1977). Hypolipidemic activity of (−)-hydroxycitrate, Lipids, 12: 1-9]. The rats were killed 30 min later by decapitation. In vivo rates of fatty acid synthesis were determined in liver, [A. C. Sullivan, J. Triscari, J. G. Hamilton and J. A. Ontko (1977). Hypolipidemic activity of (−)-hydroxycitrate, Lipids, 12: 1-9]. Data are expressed as μmoles $^3$H$_2$O or nmoles[$^{14}$C]alanine converted per g wet tissue per 30 min.

Where indicated serums were analyzed for triglycerides, [E. J. Sampson, L. M. Demers and A. F. Krieg (1975). Faster enzymatic procedure for serum triglycerides, Clinical Chemistry, 21: 1983-1985], cholesterol, [C. C. Allain, L. Poon. S. G. Chan, W. Richmond and P. Fu (1974). Enzymatic determination of total serum cholesterol, Clinical Chemistry, 20: 470-475] and glucose, [R. Konig, H. Dauwalder and R. Richterich (1971). Vergleichende Bestimmungen der Uringlucosekonzentration mit der Polarimetrie und einer enzymatischen Methode (Hexokinase/Glucose-6-Phosphat-Dehydrogenase), Schweiz. Med. Wschr., 101: 860-866] by enzymatic procedures.

The results are summarized in the following tables:

TABLE 4

EFFECT OF DINITRODESCARBOXYLASALOCID[a] ON IN VIVO HEPATIC FATTY ACID SYNTHESIS IN MEAL-FED CHARLES RIVER RATS

| Treatment | Dose mg/kg, p.o. | Food Consumption g | Fatty Acid Synthesis μmoles $^3H_2O$ converted[b] | Fatty Acid Synthesis nmoles [$^{14}C$]alanine converted[b] | Serum Cholesterol mg/100 ml | Serum Triglycerides mg/100 ml | Serum Glucose mg/100 ml |
|---|---|---|---|---|---|---|---|
| Experiment 1 | | | | | | | |
| Control (10)[c] | — | 14.0 ± 0.6 | 31.0 ± 2.4 | 435 ± 44 | 83 ± 4 | 57 ± 5 | 158 ± 6 |
| Dinitrodescarboxylasalocid (6) | 240 | 11.0 ± 0.8* | 17.1 ± 3.5* | 250 ± 87* | 85 ± 7 | 42 ± 5 | 194 ± 9* |
| Experiment 2 | | | | | | | |
| Control (12) | — | 13.0 ± 0.5 | 30.3 ± 3.1 | 974 ± 85 | 74 ± 4 | 51 ± 4 | 159 ± 5 |
| Dinitrodescarboxylasalocid (7) | 60 | 8.8 ± 1.0* | 17.0 ± 3.1* | 711 ± 130 | 84 ± 3 | 40 ± 4 | 165 ± 6 |
| Dinitrodescarboxylasalocid (7) | 120 | 10.7 ± 1.0* | 18.7 ± 2.1* | 696 ± 80* | 82 ± 6 | 31 ± 2* | 168 ± 7 |
| Dinitrodescarboxylasalocid (7) | 240 | 9.4 ± 1.1* | 12.6 ± 1.4* | 510 ± 64* | 76 ± 7 | 31 ± 5* | 183 ± 4* |

[a]Sodium salt.
[b]μmoles $^3H_2O$ or nmoles [$^{14}C$]alanine converted to fatty acids per 1 g liver per 30 min. Results are expressed as the mean ± SE.
[c]Number of rats per group indicated in parenthesis.
*Significantly different from control $P \leq 0.05$.

TABLE 5

EFFECT OF DINITRODESCARBOXYLASALOCID[a] AND MONENSIN[a] ON IN VIVO HEPATIC FATTY ACID SYNTHESIS IN MEAL-FED CHARLES RIVER RATS

| Treatment[b] | Dose mg/kg, i.p. | Food Consumption g | Fatty Acid Synthesis μmoles $^3H_2O$ converted[c] | Fatty Acid Synthesis nmoles [$^{14}C$]alanine converted[c] |
|---|---|---|---|---|
| Control | — | 16.1 ± 1.5 | 25.9 ± 3.5 | 395 ± 65 |
| Dinitrodescarboxylasalocid | 60 | 15.7 ± 0.4 | 12.5 ± 2.1* | 208 ± 42* |
| Monensin | 60 | 16.1 ± 1.4 | 14.8 ± 4.0* | 209 ± 64* |

[a]Sodium salt.
[b]There were six rats in each group.
[c]μmoles $^3H_2O$ or nmoles [$^{14}C$]alanine converted to fatty acids per 1 g liver in 30 min. Results are expressed as the mean ± SE.
*Significantly different from control $P \leq 0.05$.

TABLE 6

INHIBITION OF CORN OIL ABSORPTION BY BROMOLASALOCID AND DINITRODESCARBOXYLASALOCID

| Treatment | Dose mg/kg p.o. | Area under curve | % of control |
|---|---|---|---|
| Experiment 1 | | | |
| Control | — | 1100 | 100 |
| Bromolasalocid[a] | 145 | 704* | 64 |
| Bromolasalocid[b] | 325 | 660* | 60 |
| Bromolasalocid[c] | 140 | 659* | 60 |
| Experiment 2 | | | |
| Control | — | 1410 | 100 |
| Dinitrodescarboxylasalocid[c] | 56 | 1213 | 86 |
| Dinitrodescarboxylasalocid[c] | 120 | 1072* | 76 |
| Dinitrodescarboxylasalocid[c] | 240 | 564* | 40 |

[a]ethanolate
[b]di-(N-methylglucamine)
[c]sodium
*Significantly different from control $P \leq 0.05$.

EXAMPLE 6

In Vivo absorption of triglycerides:

The effectiveness of compounds in reducing the intestinal absorption of triglycerides was evaluated, [K. Comai, J. Triscari and A. C. Sullivan (1978). Comparative effects of amphetamine and fenfluramine on lipid biosynthesis and absorption in the rat, Biochem. Pharma. 27: 1987–1994]. The test compound was administered by gavage in 1% gum arabic 15 min prior to corn oil administration (20 ml/kg). Control rats received 1% gum arabic. Blood samples were taken from the tails at 0, 2, 4, 6, 8, 10, and 12 hr time points in heparinized microcentrifuge tubes. Plasma triglycerides were determined and are expressed as mg triglyceride per 100 ml of serum, [E. J. Sampson, L. M. Demers and A. F. Krieg (1975). Faster enzymatic procedure for serum triglycerides, Clinical Chem., 21:1983–1985[, and plotted as curves. Areas under the absorption curves were determined using a computer program based on the statistical method of Grubbs, [F. E. Grubbs (1969). Procedures for detecting outlying observations in samples, Technometrics, 11: 1–21].

The following table sets forth the numerical values of the areas under the curves as plotted.

EXAMPLE 7

Five day experiments:

A five day two hour meal model was developed to evaluate the effects of lipase inhibitors in vivo. [$^{14}C$]-triolein and [$^3H$] cholesterol were included in the 10% corn oil meal on days one and five. Test compound was administered as a dietary admix. Compound was first mixed into the fat component of the diet before the dry components were added. Food consumption and body weight gain were determined. Feces were collected from day two to day four. Rats were killed on day five and the small intestine and contents were removed for analysis.

Feces were analyzed for $^{14}C$ and $^3H$ content and fat absorption, [K. Comai, J. Triscari, and A. C. Sullivan (1978). Differences between lean and obese Zucker rats: The effect of poorly absorbed dietary lipid on energy intake and body weight gain, J. Nutr. 108: 826–835. The methods used, [K. Comai, J. Triscari, and A. C. Sullivan (1978). Differences between lean and obese Zucker rats: The effect of poorly absorbed dietary lipid on energy intake and body weight gain, J. Nutr., 108: 826–835], were a modification of the method of Miettinen et al., [T. A. Miettinen, E. H. Ahrens, Jr., and S. M. Grundy (1965). Quantitative isolation and gas liquid chromatographic analysis of total dietary and fecal neutral steroids, J. Lipid Res., 6: 411-424]. The lipids from the intestinal contents were extracted into hexane after acidification to pH 2.0 with 5 N HCl. The extracted contents were analyzed for $^{14}C$ and $^3H$ lipid by scintillation counting in LSC complete scintillation cocktail (Yorktown Research, South Hackensack, N.J.).

The following tables set forth the calculated values:

Where indicated serums were analyzed for triglycerides, [E. J. Sampson, L. M. Demers and A. F. Krieg (1975). Faster enzymatic procedure for serum triglycerides, Clinical Chemistry, 21: 1983-1985], cholesterol, [C. C. Allain, L. Poon, S. G. Chan, W. Richmond and P. Fu (1974). Enzymatic determination of total serum cholesterol, Clinical Chemistry, 20: 470-475] and glucose, [R. Konig, H. Dauwalder and R. Richterich (1971). Vergleichende Bestimmungen der Urin-

TABLE 7

EFFECTIVENESS OF DINITRODESCARBOXYLASALOCID[a] IN THE FIVE DAY TWO HOUR MEAL MODEL[b]

| Treatment | Dose mg/kg | BWG[c] g | Food Consumption g/day | Fat Absorption % | $^{14}C$ in Feces % of ingested | $^3H$-Cholesterol in Feces % of ingested |
|---|---|---|---|---|---|---|
| Control | — | 5 ± 2 | 9.6 ± 0.5 | 96.7 ± 0.2 | 1.6 ± 0.2 | 36.0 ± 1.3 |
| Dinitrodescarboxylasalocid | 120 | −1 ± 3* | 7.9 ± 0.6* | 95.6 ± 0.5 | 2.4 ± 0.7 | 28.6 ± 3.9 |
| Dinitrodescarboxylasalocid | 240 | −3 ± 2* | 7.2 ± 0.5* | 92.8 ± 0.7* | 4.4 ± 0.8* | 34.1 ± 2.6 |

[a]Sodium salt.
[b]Rats were killed four hr after the start of the meal. Results are expressed as the mean ± SE. Nine rats per treatment group.
[c]Body weight gain.
*Significantly different from control P ≦ 0.05.

TABLE 8

EFFECT OF DINITRODESCARBOXYLASALOCID[a] ON INTESTINAL CONTENT LIPIDS IN THE FIVE DAY TWO HOUR MEAL MODEL[b]

| | | Intestinal Contents | | % of $^{14}C$-lipid | | | |
|---|---|---|---|---|---|---|---|
| Treatment | Dose mg/kg | $^{14}C$-lipid % ingested | $^3H$-cholesterol % ingested | Mono- and Diglyceride | Triglyceride | Free Fatty Acids | Cholesterol Esters |
| Control | — | 0.82 ± 0.11 | 2.3 ± 0.3 | 12.8 ± 0.8 | 8.2 ± 0.6 | 66.0 ± 1.5 | 6.8 ± 0.5 |
| Dinitrodescarboxylasalocid | 120 | 0.75 ± 0.10 | 1.7 ± 0.2 | 15.3 ± 1.3 | 9.1 ± 0.8 | 61.9 ± 1.3* | 7.7 ± 1.2 |
| Dinitrodescarboxylasalocid | 240 | 0.66 ± 0.13 | 1.2 ± 0.2* | 15.9 ± 0.9* | 10.3 ± 0.7* | 59.6 ± 2.6* | 7.1 ± 0.8 |

[a]Sodium salt.
[b]Rats were killed four hr after the start of the meal. Results are expressed as the mean ± SE. Nine rats per treatment group.
*Significantly different from control P ≦ 0.05.

EXAMPLE 8

Chronic experiments:

Chronic experiments were performed with female Charles River or female genetically obese and lean Zucker rats. Compounds were administered by oral intubation or as dietary admixes. Both meal feeding and ad libitum feeding regimens were employed. Food consumption was measured daily and body weights were determined biweekly. Dietary fat absorption was determined, [K. Comai, J. Triscari and A. C. Sullivan (1978). Differences between lean and obese Zucker rats: The effect of poorly absorbed dietary lipid on energy intake and body weight gain, J. Nutr. 108: 826-835], using a modification of the method of Miettinen et al., [T. A. Miettinen, E. H. Ahrens, Jr., and S. M. Grundy (1965). Quantitative isolation and gas liquid chromatographic analysis of total dietary and fecal neutral steroids, J. Lipid Res., 6: 411-424]. At termination the carcasses were analyzed for fat, [A. C. Sullivan, J. Triscari, J. G. Hamilton and O. N. Miller (1974). Effect of (−)-hydroxycitrate upon the accumulation of lipid in the rat: II. Appetite, Lipids, 9: 129-134], and protein content, [Kjeldahl Nitrogen. Hawk's Physiological Chemistry, 14th ed., pp. 1214-1215].

glucosekonzentration mit der Polarimetrie und einer enzymatischen Methode (Hexokinase/Glucose-6-Phosphat-Dehydrogenase), Schweiz. Med. Wschr., 101: 860-866], by enzymatic procedures and free fatty acids, [C. Dalton and C. Kowalski (1967). Automated colorimetric determination of free fatty acids in biologic fluids, Clinical Chemistry, 13: 744-751], by a Colorimetric procedure. Serum immunoreactive insulins were determined by radioimmunoassay, [G. F. Bryce, P. R. Johnson, A. C. Sullivan, J. S. Stern (1977). Insulin and glucagon: Plasma levels and pancreatic release in the gentically obese Zucker rat, Hormone and Metabolic Research, 9:366-370].

Figure 2:
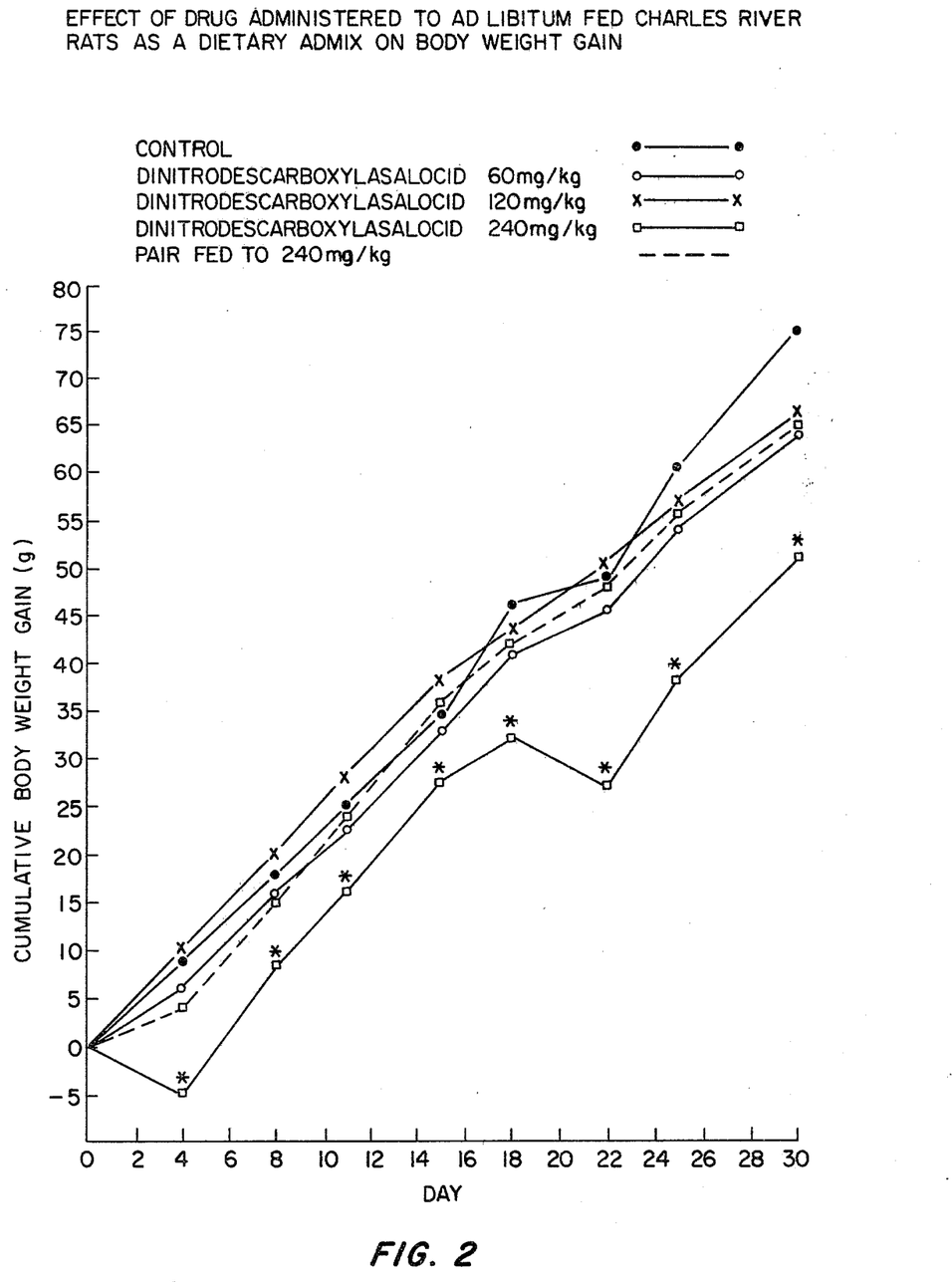

FIG. 2 sets forth body weight gain values of rats matched for initial body weight and pair fed 10% corn oil diet without dinitrodescarboxylasalocid and three groups of pair fed rats receiving 60, 120 and 240 mg/kg of dinitrodescarboxylasalocid as dietary admixes for 31 days respectively. Body weight gain compared to controls and the respective pairfed groups was reduced significantly only at the 240 mg/kg dose. Additional data for the rats described in FIG. 2 are set forth in Tables 9, 10 and 11. Tables 12 and 13 describe the effects of dinitrodescarboxylasalocid (150 mg/kg b.i.d. by oral intubation) in genetically obese and lean Zucker rats for 21 days.

TABLE 9

EFFECT OF DINITRODESCARBOXYLASALOCID[a] ADMINISTERED AS A DIETARY ADMIX (EQUIVALENT TO 60, 120 AND 240 MG/KG) TO FEMALE CHARLES RIVER RATS FED AD LIBITUM A 10% CORN OIL DIET FOR 31 DAYS[b]

| Treatment | Dose mg/kg | Body Weight Gain initial g | final g | gain g | Food Consumption g/day | Food Efficiency g gained/g consumed | Fat Absorption % |
|---|---|---|---|---|---|---|---|
| Control | — | 190 ± 3 | 262 ± 9 | 74 ± 7 | 18.1 ± 0.6 | 0.126 ± 0.009 | 95.7 ± 0.5 |
| Dinitrodescarboxylasalocid | 60 | 191 ± 3 | 255 ± 8 | 64 ± 6 | 17.4 ± 0.6 | 0.115 ± 0.010 | 95.6 ± 0.6 |
| Dinitrodescarboxylasalocid | 120 | 190 ± 3 | 256 ± 10 | 66 ± 8 | 19.0 ± 0.5 | 0.109 ± 0.014 | 95.8 ± 0.6 |
| Dinitrodescarboxylasalocid | 240 | 195 ± 4 | 246 ± 4 | 51 ± 3*+ | 17.6 ± 0.5 | 0.083 ± 0.011*+ | 88.1 ± 1.7*+ |
| pair-fed to 60 mg/kg | — | 191 ± 3 | 251 ± 4 | 60 ± 5 | 15.2 ± 0.1 | 0.111 ± 0.010 | 95.1 ± 0.5 |
| pair-fed to 120 mg/kg | — | 190 ± 4 | 257 ± 9 | 67 ± 6 | 14.7 ± 0.6 | 0.141 ± 0.022 | 94.2 ± 0.5* |
| pair-fed to 240 mg/kg | — | 195 ± 3 | 260 ± 6 | 65 ± 5 | 15.2 ± 0.3 | 0.133 ± 0.007 | 94.2 ± 0.5* |

[a] Sodium salt.
[b] Results are expressed as the mean ± SE. Eight rats per treatment group.
*Significantly different from control $P \leq 0.05$.
+Significantly different from pair-fed control $P \leq 0.05$.

TABLE 10

EFFECT OF DINITRODESCARBOXYLASALOCID[a] ADMINISTERED AS A DIETARY ADMIX (EQUIVALENT TO 60, 120 AND 240 MG/KG) TO FEMALE CHARLES RIVER RATS FED AD LIBITUM A 10% CORN OIL DIET ON CARCASS PROTEIN AND FAT[b]

| Treatment | Dose mg/kg | Carcass Protein g | % carcass weight | Carcass Fat g | % carcass weight |
|---|---|---|---|---|---|
| Control | — | 66.9 ± 2.7 | 27.2 ± 1.2 | 46.2 ± 5.1 | 18.4 ± 1.8 |
| Dinitrodescarboxylasalocid | 60 | 63.2 ± 5.6 | 26.9 ± 2.4 | 40.4 ± 5.6 | 16.9 ± 1.9 |
| Dinitrodescarboxylasalocid | 120 | 60.6 ± 3.0 | 25.6 ± 0.6 | 27.1 ± 3.2* | 11.1 ± 0.9*+ |
| Dinitrodescarboxylasalocid | 240 | 63.8 ± 1.9 | 27.8 ± 0.6 | 25.8 ± 2.0*+ | 11.3 ± 0.8*+ |
| Pair-fed to 60 mg/kg | — | 68.4 ± 2.8 | 29.1 ± 1.2 | 35.5 ± 2.3 | 15.1 ± 1.0 |
| Pair-fed to 120 mg/kg | — | 62.4 ± 1.8 | 26.0 ± 0.8 | 36.0 ± 3.3 | 15.0 ± 0.8 |
| Pair-fed to 240 mg/kg | — | 69.8 ± 2.2 | 28.7 ± 1.1 | 41.2 ± 3.1 | 16.9 ± 1.2 |

[a] Sodium salt.
[b] Results are expressed as the mean ± SE. Eight rats per treatment group.
*Significantly different from control $P \leq 0.05$
+Significantly different from pair-fed control $P \leq 0.05$

TABLE 11

SERUM PARAMETERS OF RATS FED A 10% CORN OIL DIET FOR 31 DAYS CONTAINING DINITRODESCARBOXYLASALOCID[a] EQUIVALENT TO 60, 120 and 240 MG/KG BODY WEIGHT[b]

| Treatment | Dose mg/kg | Glucose mg/100 ml | Cholesterol mg/100 ml | Triglycerides mg/100 ml | Free Fatty Acids μeq/l | IRI[c] ng/ml |
|---|---|---|---|---|---|---|
| Control | — | 173 ± 5 | 92 ± 5 | 84 ± 3 | 493 ± 61 | 2.0 ± 0.3 |
| Dinitrodescarboxylasalocid | 60 | 173 ± 5 | 106 ± 6+ | 73 ± 3*+ | 469 ± 46 | 1.8 ± 0.2 |
| Dinitrodescarboxylasalocid | 120 | 164 ± 5 | 88 ± 6 | 64 ± 5* | 425 ± 45 | 2.0 ± 0.2 |
| Dinitrodescarboxylasalocid | 240 | 155 ± 8 | 155 ± 9+ | 51 ± 4*+ | 423 ± 61 | 1.7 ± 0.2 |
| Pair-fed to 60 mg/kg | — | 164 ± 2 | 87 ± 5 | 61 ± 9 | 525 ± 56 | 1.8 ± 0.2 |
| Pair-fed to 120 mg/kg | — | 158 ± 5* | 82 ± 5 | 71 ± 9 | 530 ± 47 | 1.7 ± 0.2 |
| Pair-fed to 240 mg/kg | — | 164 ± 7 | 93 ± 5 | 73 ± 10 | 546 ± 31 | 2.1 ± 0.5 |

[a] Sodium salt.
[b] Results are expressed as the mean ± SE. Eight rats per treatment group.
[c] Immunoreactive insulin.
*Significantly different from control $P \leq 0.05$.
+Significantly different from pair-fed control $P \leq 0.05$.

TABLE 12

EFFECT OF DINITRODESCARBOXYLASALOCID[a] ADMINISTERED (150 MG/KG, B.I.D. DAILY FOR 21 DAYS) TO OBESE AND LEAN FEMALE ZUCKER RATS FED AD LIBITUM A 10% CORN OIL DIET[b]

| Treatment | Genotype[c] | Initial Body Weight g | Final Body Weight g | Body Weight Gain g | Food Consumption g/day | Fecal Weight g | Fat Absorption % |
|---|---|---|---|---|---|---|---|
| Control | fa/fa | 294 ± 14 | 364 ± 14 | 72 ± 5 | 21.0 ± 0.3 | 1.6 ± 0.1 | 93.4 ± 0.6 |
| Dinitrodescarboxylasalocid | fa/fa | 293 ± 12 | 352 ± 12 | 61 ± 6 | 19.5 ± 0.9 | 2.1 ± 0.1* | 93.0 ± 1.1 |
| Control | Fa/— | 177 ± 7 | 204 ± 6 | 27 ± 4 | 18.6 ± 0.4 | 1.5 ± 0.1 | 93.5 ± 0.7 |
| Dinitrodescarboxylasalocid | Fa/— | 178 ± 7 | 202 ± 5 | 20 ± 4 | 16.8 ± 0.8 | 1.6 ± 0.1 | 90.1 ± 0.9* |

SERUM PROFILES

TABLE 12-continued
EFFECT OF DINITRODESCARBOXYLASALOCID[a] ADMINISTERED (150 MG/KG, B.I.D. DAILY FOR 21 DAYS) TO OBESE AND LEAN FEMALE ZUCKER RATS FED AD LIBITUM A 10% CORN OIL DIET[b]

|  |  | Cholesterol mg/100 ml | Triglycerides mg/100 ml | Free Fatty Acids μeq/l | Glucose mg/100 ml | IRI[d] ng/ml |
|---|---|---|---|---|---|---|
| Control | fa/fa | 151 ± 15 | 400 ± 83 | 898 ± 112 | 178 ± 7 | 12.1 ± 2.2 |
| Dinitrodescar-boxylasalocid | fa/fa | 168 ± 6 | 178 ± 19* | 668 ± 59 | 201 ± 12 | 8.3 ± 0.6 |
| Control | Fa/— | 76 ± 2 | 99 ± 11 | 427 ± 27 | 177 ± 7 | 1.6 ± 0.1 |
| Dinitrodescar-boxylasalocid | Fa/— | 84 ± 7 | 71 ± 5* | 519 ± 58 | 154 ± 6* | 0.5 ± 0.1* |

[a]Sodium salt.
[b]Results are expressed as the mean ± SE; nine rats per group. Rats dosed at 8:30 a.m. and 4 p.m.
[c]fa/fa = obese genotype, Fa/— = lean genotype.
[d]IRI = immunoreactive insulin.
*Significantly different from control $P \leq 0.05$.

TABLE 13
EFFECT OF DINITRODESCARBOXYLASALOCID[a] ADMINISTERED (150 MG/KG, BI.I.D. DAILY FOR 21 DAYS) TO OBESE AND LEAN FEMALE ZUCKER RATS FED AD LIBITUM A 10% CORN OIL DIET ON CARCASS PROTEIN AND FAT[b]

| Treatment | Genotype[c] | Carcass Protein[d] g | % carcass weight | Carcass Fat[e] g | % carcass weight |
|---|---|---|---|---|---|
| Control | fa/fa | 66.2 ± 6.1 | 19.3 ± 1.1 | 205 ± 12 | 59.2 ± 1.9 |
| Dinitrodescarboxylasalocid | fa/fa | 66.8 ± 2.5 | 19.4 ± 1.4 | 183 ± 8 | 53.8 ± 0.8* |
| Control | Fa/— | 49.0 ± 3.7 | 26.0 ± 1.1 | 23.0 ± 1.1 | 11.7 ± 0.5 |
| Dinitrodescarboxylasalocid | Fa/— | 48.4 ± 3.1 | 26.3 ± 0.5 | 18.8 ± 1.8* | 10.3 ± 0.8 |

[a]Sodium salt.
[b]Results are expressed as the mean ± SE. Nine rats per treatment group.
[c]fa/fa = obese genotype, Fa/— = lean genotype.
[d]Analyses were performed for four rats from each group.
[e]Analyses were performed for all rats in each group.
*Significantly different from control $P \leq 0.05$.

EXAMPLE 9

CAPSULE FORMULATION

| Item | Ingredients | 1 mg | 5 mg | 25 mg | 50 mg | 100 mg | 200 mg |
|---|---|---|---|---|---|---|---|
| 1. | dinitrodescarboxy-lasalocid | 1 | 5 | 25 | 50 | 100 | 200 |
| 2. | Lactose | 204 | 295 | 375 | 155 | 200 | 140 |
| 3. | Starch | 30 | 35 | 30 | 30 | 35 | 40 |
| 4. | Talc | 15 | 15 | 20 | 15 | 15 | 20 |
|  | Weight of tablet | 250 mg | 350 mg | 450 mg | 250 mg | 350 mg | 400 mg |

Procedure:
1. Mill Items 1-3 in a suitable mixer.
2. Add talc and mix well.
3. Encapsulate on suitable equipment.

EXAMPLE 10

TABLET FORMULATION (Direct Compression)

| Item | Ingredients | 1 mg | 5 mg | 25 mg |
|---|---|---|---|---|
| 1. | dinitrodescarboxylasalocid | 1 | 5 | 25 |
| 2. | Lactose | 221 | 217 | 181 |
| 3. | Avicel | 45 | 45 | 55 |
| 4. | Direct Compression Starch | 30 | 30 | 35 |
| 5. | Magnesium Stearate | 3 | 3 | 4 |

TABLET FORMULATION (Direct Compression) -continued

| Item | Ingredients | 1 mg | 5 mg | 25 mg |
|---|---|---|---|---|
|  | Weight of tablet | 300 mg | 300 mg | 300 mg |

Procedure:
1. Mix Item 1 with an equal amount of lactose. Mix well.
2. Mix with Items 3 and 4, and the remaining amount of Item 2. Mix well.
3. Add magnesium stearate and mix for 3 minutes.
4. Compress on a suitable press equipped with appropriate punches.

EXAMPLE 11

TABLET FORMULATION (Wet granulation)

| Item | Ingredients | 1 mg | 5 mg | 25 mg | 50 mg | 100 mg | 200 mg |
|---|---|---|---|---|---|---|---|
| 1. | dinitrodescarboxy-lasalocid | 1 | 5 | 25 | 50 | 100 | 200 |
| 2. | Lactose | 202 | 232 | 280 | 153 | 187 | 171 |

-continued
TABLET FORMULATION (Wet granulation)

| Item | Ingredients | 1 mg | 5 mg | 25 mg | 50 mg | 100 mg | 200 mg |
|------|-------------|------|------|-------|-------|--------|--------|
| 3. | Modified Starch | 25 | 35 | 55 | 25 | 35 | 45 |
| 4. | Pregelatinized Starch | 20 | 25 | 35 | 20 | 25 | 30 |
| 5. | Distilled water q.s. | — | — | — | — | — | — |
| 6. | Magnesium Stearate | 2 | 3 | 5 | 2 | 3 | 4 |
| | Weight of tablet | 250 mg | 300 mg | 400 mg | 250 mg | 350 mg | 450 mg |

Procedure:
1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

We claim:

1. A method of treating high triglyceride levels in warm blooded animals in need of such treatment which comprises orally administering to such warm blooded animals from 1 mg/kg/day to 300 mg/kg/day of polyether compound with ionophore activity sufficient to inhibit fatty acid synthesis or the activity of pancreatic lipase.

2. The method of claim 1 wherein the dose administered is from about 1 mg/kg/day to 100 mg/kg/day.

3. The method of claim 1 wherein the polyether compound is dinitrodescarboxylasalocid or pharmaceutically acceptable salts thereof.

4. The method of claim 3 wherein the polyether compound is dinitrodescarboxylasalocid or pharmaceutically acceptable salts thereof.

5. The method of claim 1 wherein the polyether compound is lasalocid or the pharmaceutically acceptable salts and esters thereof.

6. The method of claim 1 wherein the polyether compound is selected from the group consisting of the chlorolasalocid, bromolasalocid, iodolasalocid and nitrolasalocid.

7. The method of claim 1 wherein the polyether compound is isolasalocid.

8. The method of claim 1 wherein the polyether compound is selected from the group consisting of X-14547A, A-130 A, A-204, BL-580, A-28086, X-206, ionomycin, lysocellin and nigericin.

9. The method of claim 1 wherein the polyether compound is monensin.

10. The method of claim 1 wherein the polyether compound is A-23187.

11. The method of claim 1 wherein the polyether compound is deoxy-(0–8)-epi-17-salinomycin.

12. The method of claim 1 wherein the polyether compound is lasalocid methoxime.

* * * * *